US005808665A

United States Patent [19]
Green

[11] Patent Number: 5,808,665
[45] Date of Patent: Sep. 15, 1998

[54] ENDOSCOPIC SURGICAL INSTRUMENT AND METHOD FOR USE

[75] Inventor: Philip S. Green, Redwood City, Calif.

[73] Assignee: SRI International, Menlo Park, Calif.

[21] Appl. No.: 709,965

[22] Filed: Sep. 9, 1996

Related U.S. Application Data

[63] Continuation of Ser. No. 823,932, Jan. 21, 1992, abandoned.

[51] Int. Cl.$^6$ .................................................. H04N 7/18
[52] U.S. Cl. ............................................ 348/65; 600/101
[58] Field of Search ............................... 348/61, 65, 143, 348/159, 207; 600/101, 109; 901/1, 2, 9, 30, 33, 34, 36; H04N 7/18

[56] References Cited

U.S. PATENT DOCUMENTS

| | | |
|---|---|---|
| 1,418,184 | 5/1922 | Trunick . |
| 2,815,697 | 12/1957 | Saunders-Singer ......................... 88/40 |
| 2,901,258 | 8/1959 | Brandafi . |
| 3,145,333 | 8/1964 | Pardini et al. . |
| 3,463,329 | 8/1969 | Gartner ....................................... 214/1 |
| 3,818,125 | 6/1974 | Butterfield ............................... 178/6.5 |
| 3,921,445 | 11/1975 | Hill et al. ............................... 73/133 R |
| 3,923,166 | 12/1975 | Fletcher et al. ............................ 901/2 |
| 3,934,201 | 1/1976 | Majetski ..................................... 381/14 |

(List continued on next page.)

FOREIGN PATENT DOCUMENTS

| | | |
|---|---|---|
| 0 239 409 A1 | 3/1987 | European Pat. Off. .......... A61F 9/00 |
| 0 291 292 A2 | 5/1988 | European Pat. Off. ........ F16H 21/44 |
| 0 595 291 A1 | 10/1993 | European Pat. Off. ........... B25J 9/10 |
| 2 460 762 | 1/1979 | France ............................... B25J 3/02 |
| 86 00852 | 1/1986 | France ............................. B25J 11/00 |
| 28 19 976 | 5/1978 | Germany ......................... F16M 1/00 |
| 3806190 | 9/1988 | Germany ....................... H04N 13/02 |
| 4 213 426 | 10/1992 | Germany . |
| 482 439 | 1/1970 | Switzerland . |
| 2040134 | 8/1980 | United Kingdom . |
| 2117732 | 10/1983 | United Kingdom ............... B25J 9/00 |

WO 92/16141 10/1992 WIPO .

OTHER PUBLICATIONS

A.D. Alexander, III, "Impacts of Telemation on Modern Society", *, *1st CISM–IFTO MM Symposium*, vol. 2, pp. 122–136. (Sep. 1973).

A.K. Bejczy et al, "Controlling Remote Manipulators Through Kinesthetic Coupling", 1983, *Computers in Mechanical Engineering*, pp. 48–60.

Fisher et al., "Virtual Interface Environment", 1986, *Proceedings IEEE/AIAA 7th Digital Avionics Systems Conference*, pp. 346–350.

(List continued on next page.)

*Primary Examiner*—Richard Lee
*Attorney, Agent, or Firm*—Townsend and Townsend and Crew LLP

[57] ABSTRACT

A teleoperator system with telepresence is shown which includes right and left hand controllers (72R and 72L) for control of right and left manipulators (24R and 24L) through use of a servomechanism that includes computer (42). The teleoperator system comprises a endoscope surgical instrument suited for endoscopic surgery. The surgical instrument comprises a control servomechanism which operates an insertion section. The insertion section comprises a forearm, a wrist and an end effector. The end effector is a modified surgical instrument such as retractors, electrosurgical cutters, electrosurgical coagulators, forceps, needle holders, scissors, blades and irrigators. The control section contains motors and linkages which operate the insertion section with five or more degrees of freedom. The control section inserts, retracts, pivots and rotates the forearm with four degrees of freedom about axes that all intersect adjacent a small incision through which the insertion section is introduced to the patient. The control section also pivots the wrist with at least one degree of freedom relative to the forearm and operates the end effector. The surgical manipulator provides superior flexibility in performing endoscopic procedures compared to standard rigid endoscopic instruments and is adapted for teleoperator control.

32 Claims, 9 Drawing Sheets

U.S. PATENT DOCUMENTS

| | | |
|---|---|---|
| 4,113,115 | 9/1978 | Yoshio . |
| 4,260,319 | 4/1981 | Motoda et al. . |
| 4,264,266 | 4/1981 | Trechsel . |
| 4,349,837 | 9/1982 | Hinds ........................................ 358/93 |
| 4,419,041 | 12/1983 | Rose . |
| 4,510,574 | 4/1985 | Guittet et al. ............................... 901/2 |
| 4,562,463 | 12/1985 | Lipton ....................................... 358/88 |
| 4,582,067 | 4/1986 | Silberstein ............................. 128/663 |
| 4,583,117 | 4/1986 | Lipton et al. .............................. 358/92 |
| 4,636,138 | 1/1987 | Gorman . |
| 4,651,201 | 3/1987 | Schoolman ............................... 358/98 |
| 4,744,363 | 5/1988 | Hasson . |
| 4,750,475 | 6/1988 | Yoshihashi ................................. 128/6 |
| 4,751,925 | 6/1988 | Tontarra . |
| 4,762,455 | 8/1988 | Coughlan et al. . |
| 4,808,898 | 2/1989 | Pearson . |
| 4,837,734 | 6/1989 | Ichikawa et al. ............................ 901/2 |
| 4,855,822 | 8/1989 | Narendar et al. ....................... 358/103 |
| 4,862,873 | 9/1989 | Yajima et al. ............................... 128/6 |
| 4,873,572 | 10/1989 | Miyazaki et al. . |
| 4,899,730 | 2/1990 | Stennert et al. ............................ 128/4 |
| 4,922,338 | 5/1990 | Arpino ...................................... 358/93 |
| 4,941,106 | 7/1990 | Krieger .................................... 364/513 |
| 4,942,539 | 7/1990 | McGee et al. ........................... 364/513 |
| 4,947,702 | 8/1990 | Kato . |
| 5,002,418 | 3/1991 | McCown et al. . |
| 5,020,933 | 6/1991 | Salvestro et al. . |
| 5,045,936 | 9/1991 | Lobb et al. ............................... 358/98 |
| 5,060,532 | 10/1991 | Barker . |
| 5,062,761 | 11/1991 | Glachet . |
| 5,078,140 | 1/1992 | Kwoh . |
| 5,096,236 | 3/1992 | Thony . |
| 5,141,519 | 8/1992 | Smith et al. . |
| 5,142,930 | 9/1992 | Allen et al. . |
| 5,209,747 | 5/1993 | Knoepfler .................................. 606/16 |
| 5,219,351 | 6/1993 | Teubner et al. . |
| 5,236,432 | 8/1993 | Matsen, III et al. . |
| 5,253,706 | 10/1993 | Reid . |
| 5,257,998 | 11/1993 | Ota et al. . |
| 5,260,319 | 11/1993 | Effland et al. . |
| 5,264,266 | 11/1993 | Yokoyama et al. . |
| 5,273,039 | 12/1993 | Fujiwara et al. . |
| 5,279,309 | 1/1994 | Taylor et al. . |
| 5,281,220 | 1/1994 | Blake, III . |
| 5,284,130 | 2/1994 | Ratliff . |
| 5,325,866 | 7/1994 | Krzyzanowski . |
| 5,339,799 | 8/1994 | Kami et al. . |
| 5,397,323 | 3/1995 | Taylor et al. . |
| 5,425,528 | 6/1995 | Rains et al. . |
| 5,441,505 | 8/1995 | Nakamura . |
| 5,474,566 | 12/1995 | Alesi et al. . |
| 5,480,409 | 1/1996 | Riza . |
| 5,636,138 | 6/1997 | Gilbert et al. . |

OTHER PUBLICATIONS

Hald et al., "Telepresence, Time Delay and Adaptation", *, *Spatial Displays and Spatial Instruments Proceedings of a Conference sponsored by NASA Ames Research Center and the School of Optometry, Univ. of California*, pp. 28–1 through 28–16.

Kim et al., "A Helmet Mounted Display for Telerobotics", 1988 *33 IEEE Computer Society International Conference, California*, pp. 543–547.

B. M. Jau, "Anthropomorphic Remoter Manipulator", 1991, *NASA Tech Briefs*, p. 92. (Apr. 1991).

K. Matsushima, "Servo Micro Manipulator Tiny Micro Mark–1", 1982, *4th Symposium on Theory and Practice of Robots and Manipulators*, pp. 193–201.

R. Richter, "Telesurgery may Bridge Future Gaps", 1988, *Times Tribune*, Sunday, Jan. 24, pp. A–1 and A–16.

E. H. Spain, "Stereo Advantage for a Peg–In–Hole Task Using Force–Feedback Manipulator", 1990, *Stereoscopic Displays and Applications*, pp. 244–254.

Tachi et al., "Tele–existence Master Slave System for Remote Manipulation", 1990, *Proceedings of the 29th Conference on Decision and Control*, vol. 1 of 6, pp. 85–90.

"Introduction t a New Project for The National Research Development Program (Large–Scale Project) in FY 1991—Micromachine Technology", 1991, *Agency of Industrial Science and Technology Ministry of International Trade and Industry, Japan*, pp. 1–11.

"Another Pair of Hands for Surgeon?" 1972, *The Blue Cross magazine Perspective*, p. 27.

Asada Haruhiko et al., "Development of a Direct–Drive Arm Using High Torque Brushless Motors," Chapter 7, pp. 583–599.

Guerrouad Aicha et al., "S.M.O.S.: Stereotaxical Microelemanipulator for Ocular Surgery," *IEEE Engineering in Medicine & Biology Society*, 11th Annual International Conference, 1989, Medical Applications of Robotics, Track 16: Biorobotics, pp. 879–880.

Kazerooni H., "Design and Analysis of the Statically Balanced Direct–Drive Robot Manipulator," *Robotics & Computer–Integrated Manufacturing*, 1989, vol. 6, No. 4, pp. 287–293.

Ng. W. S. et al., "Robotic Surgery," *IEEE Engineering in Medicine and Biology*, Mar. 1993, pp. 120–125.

Taubes Gary, "Surgery in Cyberspace," *Discover*, Dec. 1994, pp. 85–92.

Taylor Russell H. et al., "A Telerobotic Assistant for Laparoscopic Surgery," *Engineering in Medicine and Biology*, May–Jun. 1995, pp. 279–288.

Trevelyan James P. et al., "Motion Control for a Sheep Shearing Robot," *IEEE Robotics Research Conference*, the 1st International Symposium, Carroll, NH, USA, Conference Date: Aug. 25, 1983, Conference No. 05357, Publication by MIT Press, pp. 175–190.

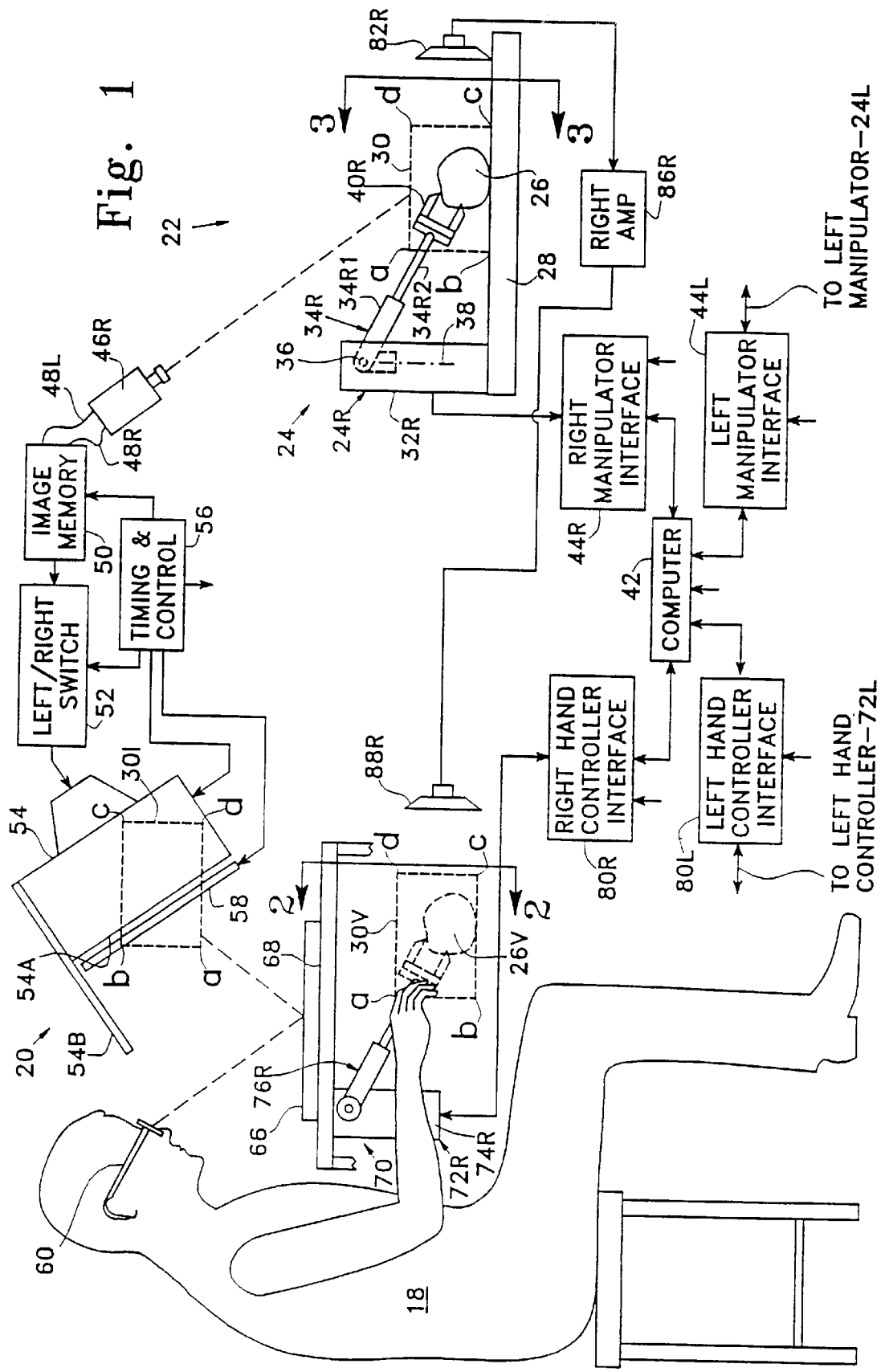

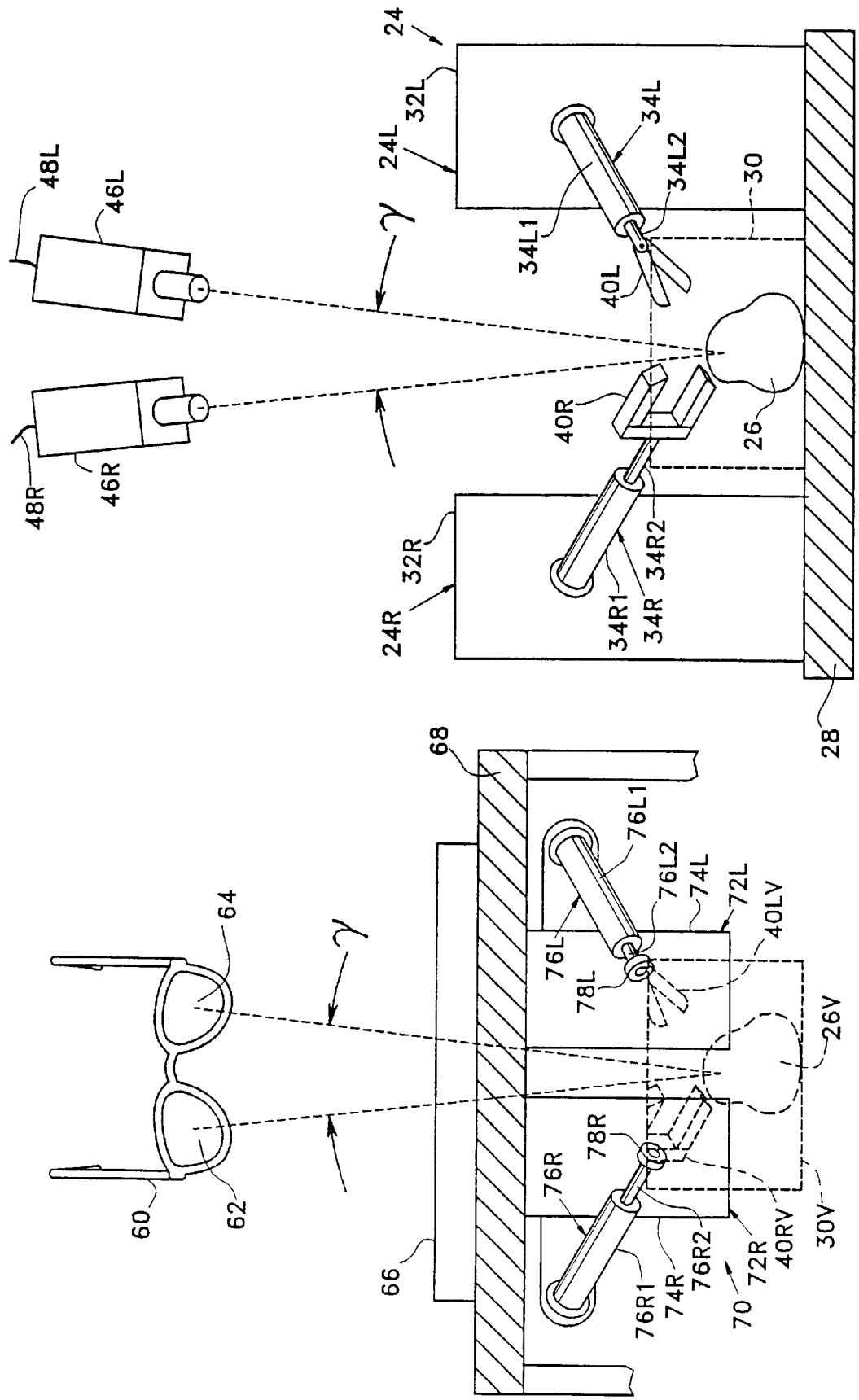

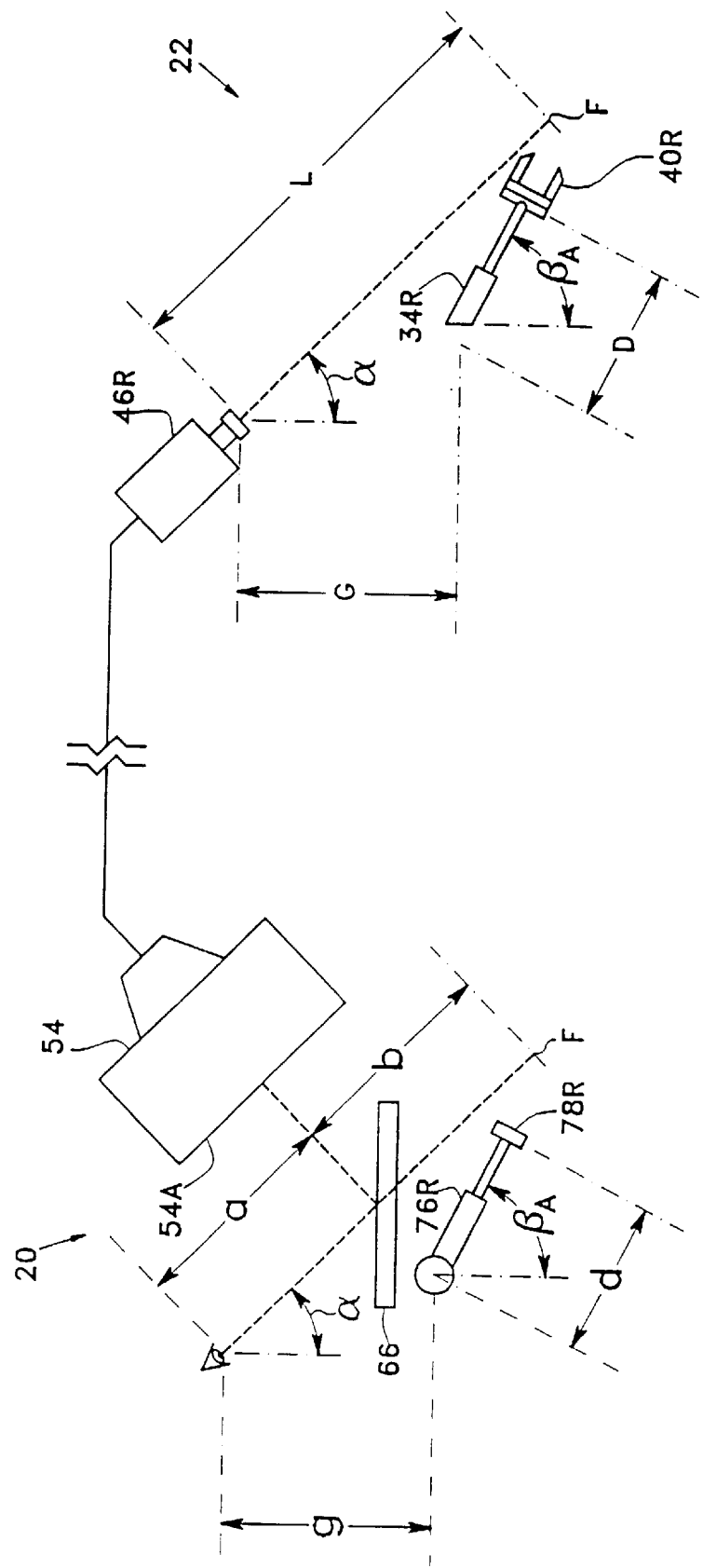

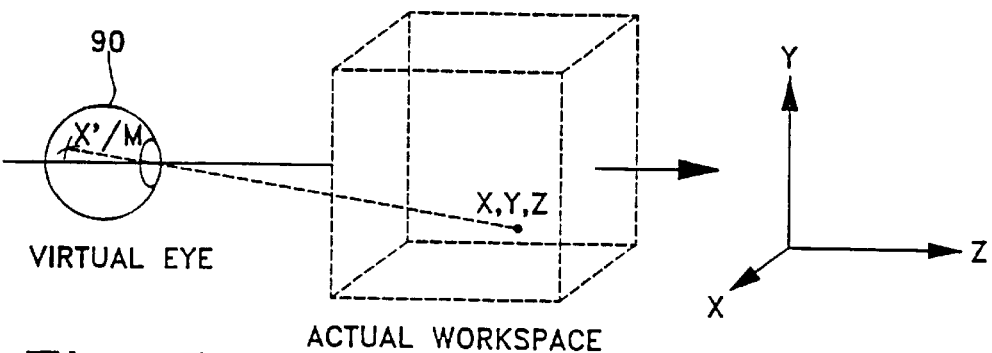
Fig. 5
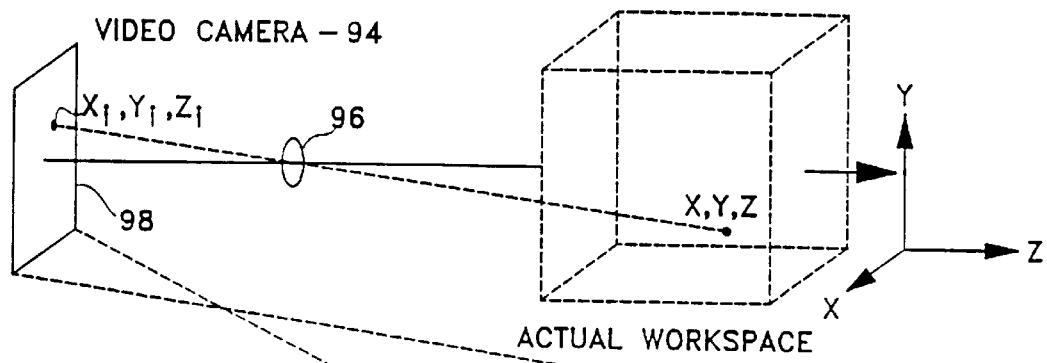
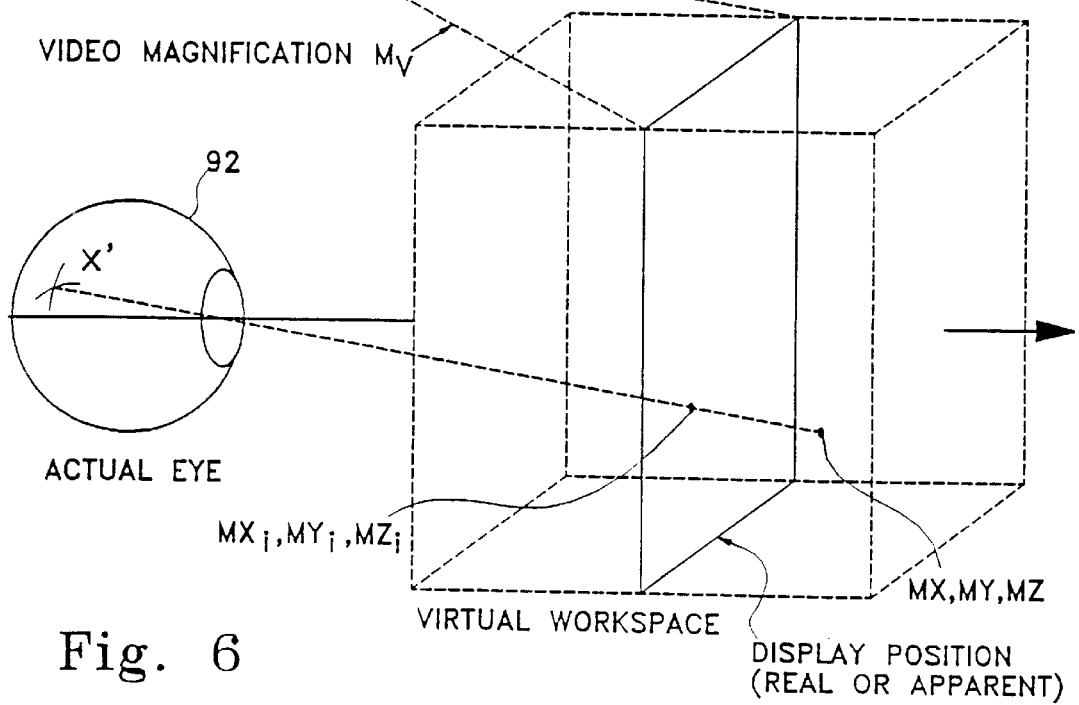
Fig. 6

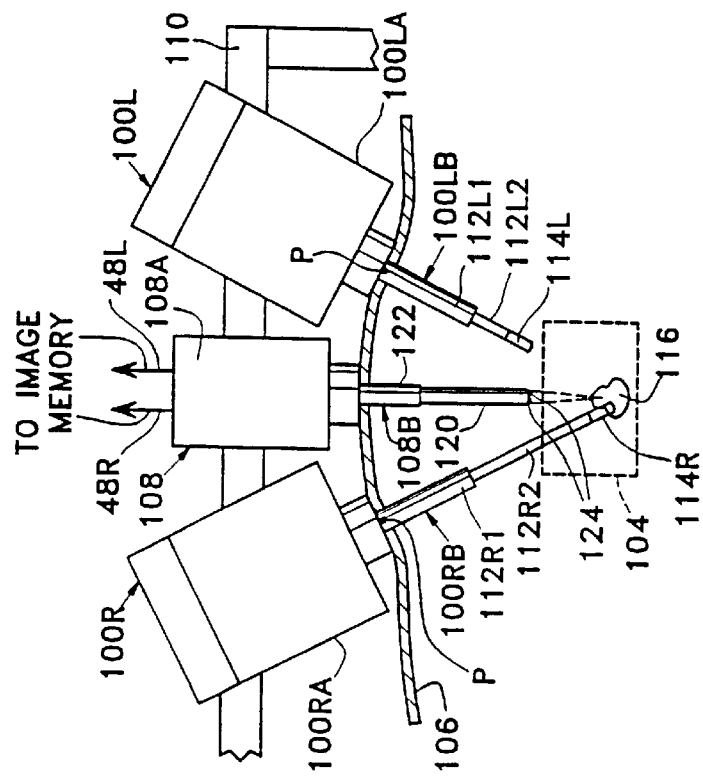
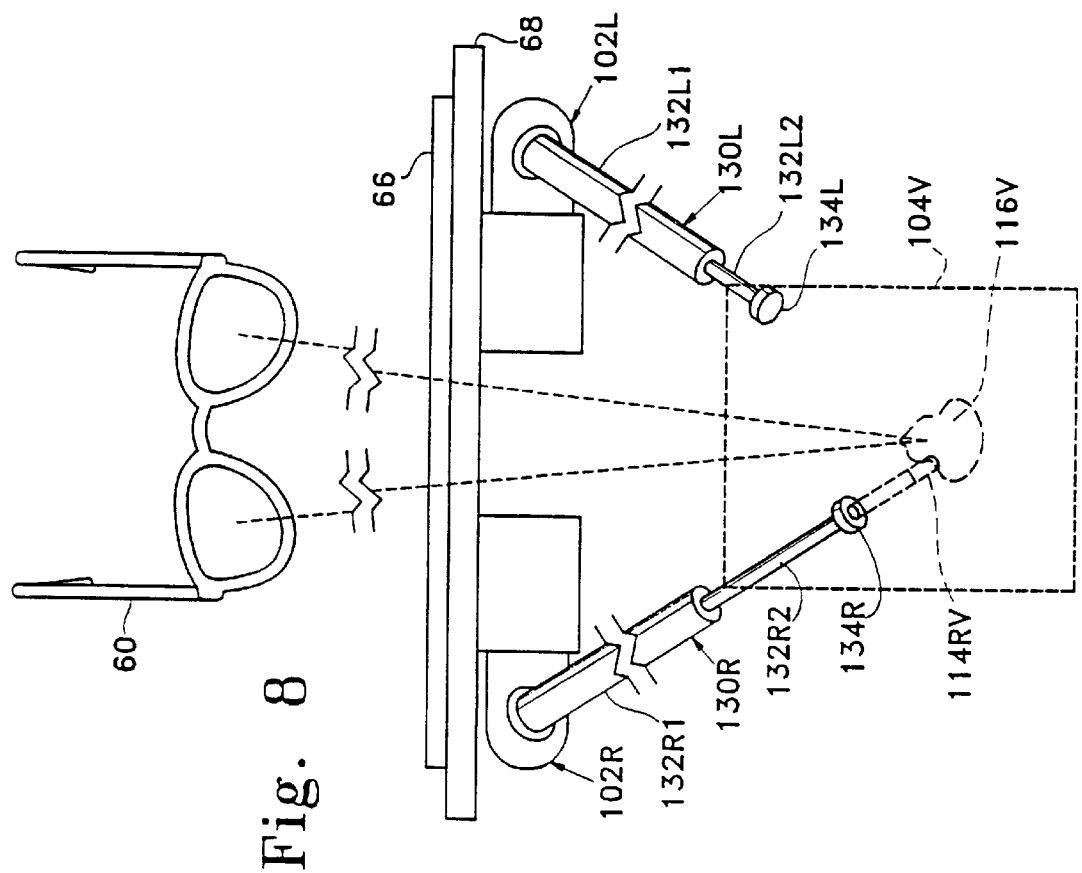
Fig. 9
Fig. 8

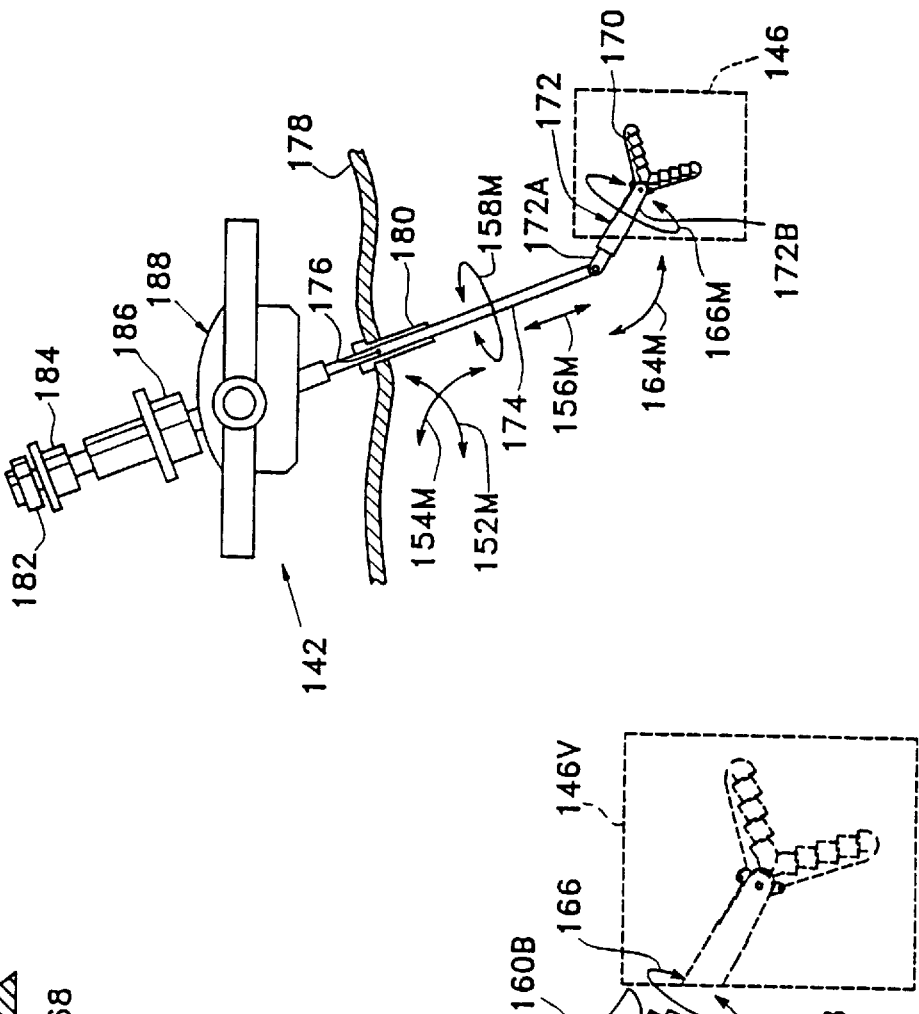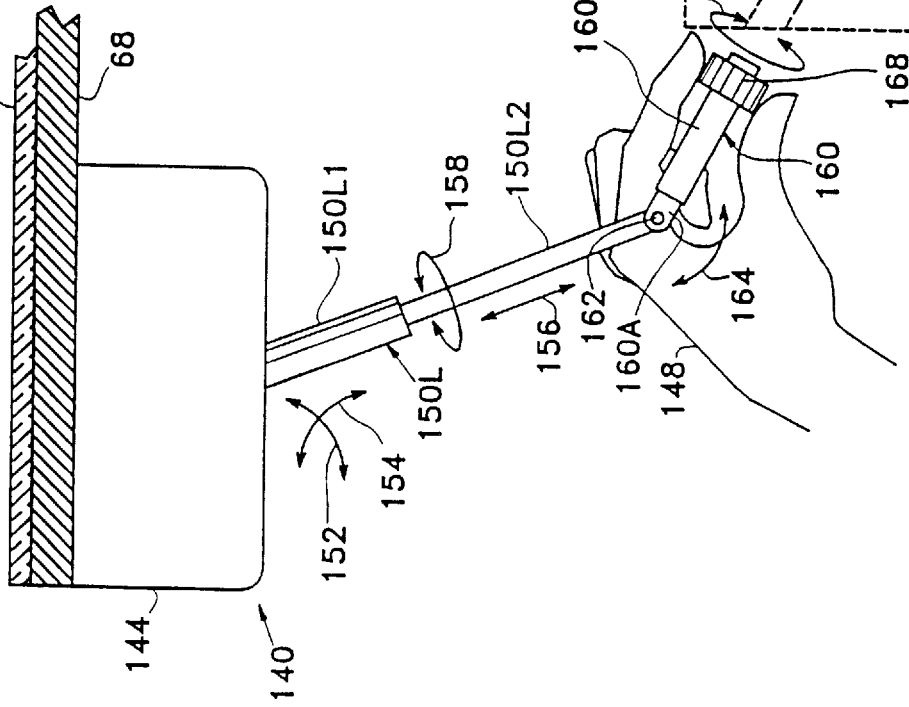

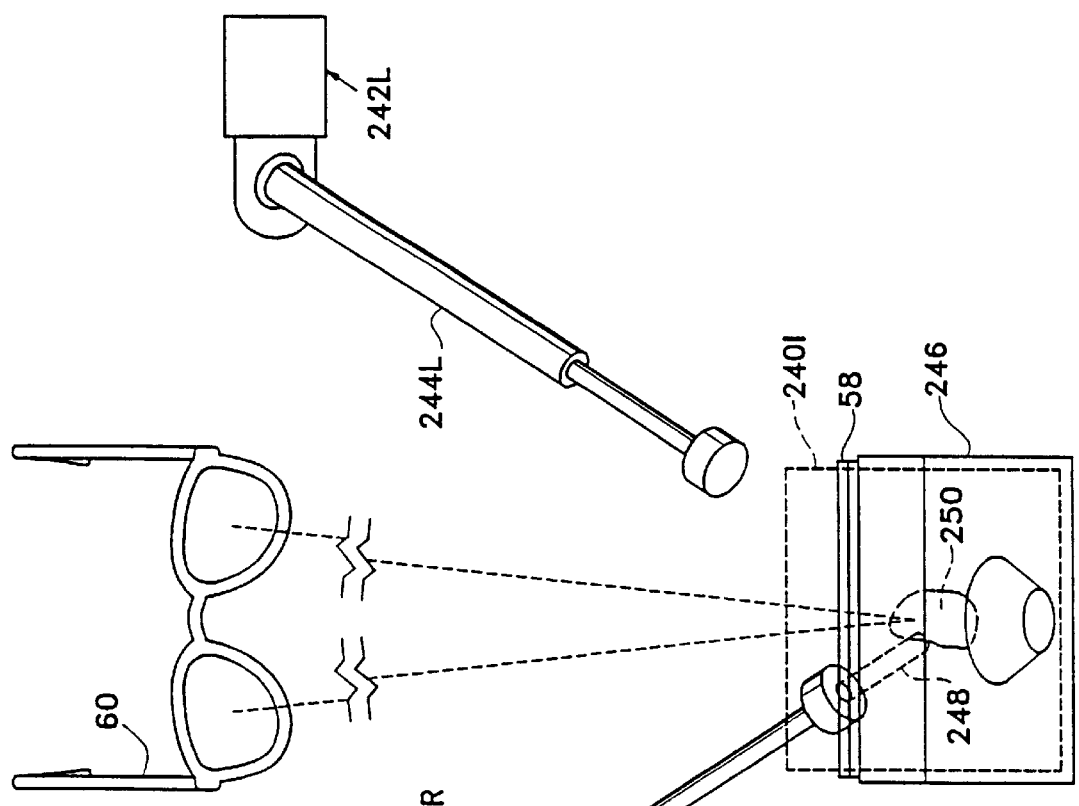
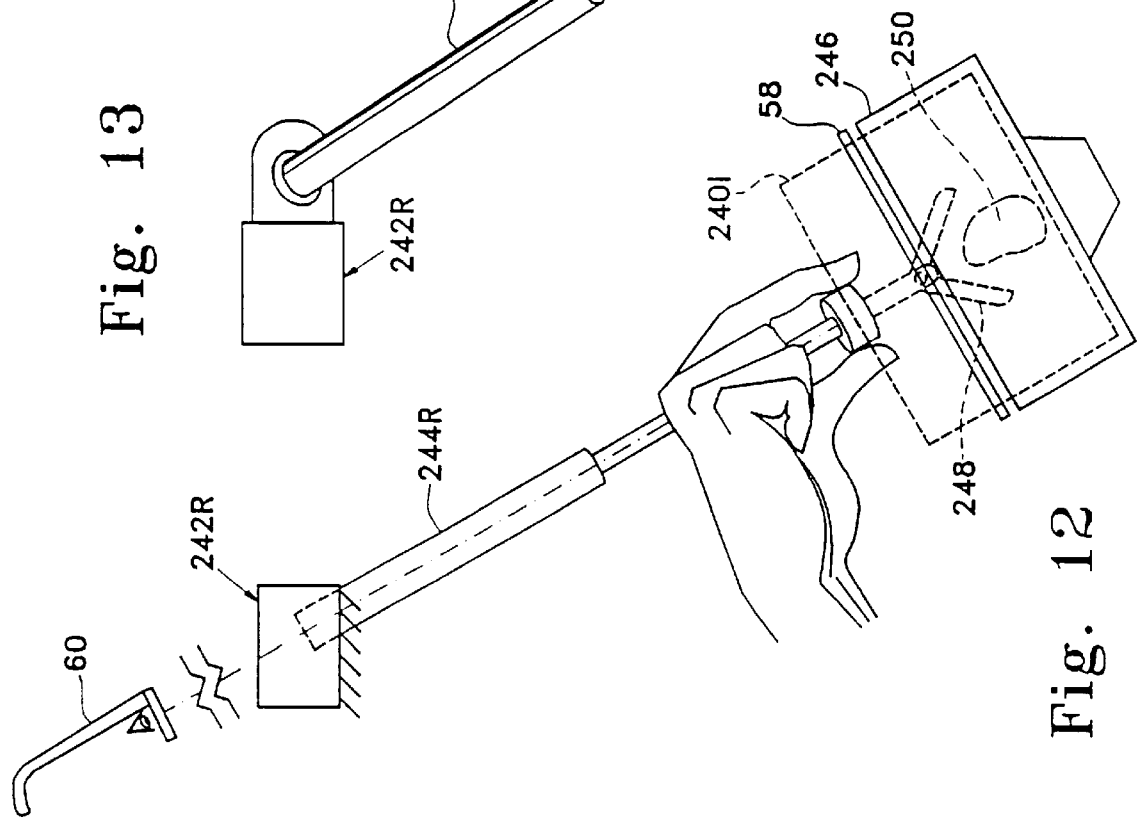
Fig. 13
Fig. 12

ENDOSCOPIC SURGICAL INSTRUMENT AND METHOD FOR USE

This is a Continuation of application Ser. No. 07/823,932 filed Jan. 21, 1992 now abandoned.

FIELD OF THE INVENTION

This invention relates generally to teleoperator method and apparatus, and particularly to those which include means for providing the operator of remote apparatus with the same sense as working directly with his hands at the worksite.

BACKGROUND OF THE INVENTION

Teleoperating, which is well known, includes the human performance of tasks at a remote location using manipulators. Telepresence includes providing the teleoperator with the same feedback and control that he would have were he actually at the worksite carrying out the operation with his own hands. Telepresence operation generally includes use of a stationary visual display, particularly a stereographic visual display of the remote workspace. Stereoscopic television systems are well known as shown, for example, in U.S. Pat. Nos. 4,562,463 and 4,583,117 and in U.K. Patent Application GB 2,040,134.

Remote manipulators employing stereoscopic TV viewing together with force feedback also are well known as shown, for example, in an article entitled, "Controlling Remote Manipulators Through Kinesthetic Coupling," Befczy et al, Computers in Mechanical Engineering, July 1983, pps. 48–60, and in an article entitled, "Stereo Advantage for a Peg-In-Hole Task Using a Force-Feedback Manipulator" by E. H. Spain, SPIE Vol. 1256 Stereoscopic Displays and Applications, 1990, pps. 244–254. In the Bejczy et al article, force-torque feedback is disclosed. Also, in U.S. Pat. No. 3,921,445, a manipulator which includes force, torque and slip sensors of a type which may be employed with the present invention is shown.

Even though the operator of prior art manipulators is provided with a stationary three-dimensional image of the workspace, and manual controllers for control of the manipulators are provided with feedback, the operator is not provided with a sense of actually being present at the worksite. The present invention is directed to a viewing arrangement for use in a remote manipulation system which substantially adds to the operator's sense of presence at the remote manipulator site.

SUMMARY AND OBJECTS OF THE INVENTION

An object of this invention is the provision of an improved teleoperator system and method which include an improved viewing system to enhance the operator's sense of presence at remote manipulators controlled by the operator from a remote location.

An object of this invention is the provision of an improved teleoperator system and method of the above-mentioned type wherein an image of manipulator end effectors for viewing by the operator are sensed by the operator as comprising an integral part of hand-controllers used by the operator to control the end effectors, thereby giving the operator a strong sense of presence at the worksite.

An object of this invention is the provision of an improved teleoperator system and method of the above-mentioned type which is well adapted for use in a wide variety of applications including military, industrial, biomedical, and the like.

The present invention includes manipulators located at a worksite and which are controlled by hand-operated means at a remote operator control station. End effectors at the manipulators are used for manipulating objects located in a workspace at the worksite, and force-torque feedback is employed for transmitting back to the operator mechanical resistance encountered by the end effectors. Stereographic visual display means provide the operator with an image of the workspace. In accordance with the present invention, the image is located adjacent the hand-operator means so that the operator looks in the direction of the hand-operated means for viewing the image adjacent the hand-operated means. Either a real or virtual image of the workspace may be provided adjacent the hand-operated means. Display means for display of real image may be located adjacent the hand-operated means for direct viewing of the real image by the operator. For display of a virtual image of the workspace, a mirror is located between the operator's eyes and the hand-operated means. In this case, display means provide a real image which is inverted from top to bottom, which inverted image is viewed via the mirror, which mirror inverts the image and provides the operator with a virtual image of the workspace, which appears to be located adjacent the hand-operated means. By locating the image of the workspace adjacent the hand-operated means the operator is provided with a sense that the end effectors and hand-operated means are substantially integral despite the fact the end effectors are located at the worksite and the hand-operated means are located at the remote operator's station. A stereophonic sound system may be included to provide the operator with stereophonic sound from the worksite. Video camera means are provided for viewing the workspace from which an image of the workspace is obtained. Various other sensors and associated responders may be located at the worksite and operator's station, respectively, for transmission of pressure, tactile, heat, vibration and similar information for enhance telepresence operation.

Depending upon the application, different scaling may be provided in the transmission of information between the operator's station and worksite. For example, for microassembly, microsurgery and like operations involving small part manipulation, optical and/or video magnification may be employed to provide an enlarged 3-dimensional image for viewing by the operator. With similar scaling between the hand operated means and manipulators, the perception of the operator is substantially that which a miniature operator would have were he at the worksite.

BRIEF DESCRIPTION OF THE DRAWINGS

The invention, together with other objects and advantages thereof, will be better understood from the following description considered with the accompanying drawings. It will be understood that the drawings are for purposes of illustration and example only, and that the invention is not limited thereto. In the drawings, wherein like reference characters refer to the same parts in the several views, FIG. 1 is a diagrammatic showing of a teleoperator system embodying the present invention including side elevational views of a worksite and remote control operator's station;

FIG. 2 is an enlarged rear elevational view of the operator's station taken substantially along line 2—2 of FIG. 1;

FIG. 3 is an enlarged rear elevational view of the worksite taken substantially along line 3—3 of FIG. 1;

FIG. 4 is a simplified side elevational view which is similar to FIG. 1 and showing dimensional relationships between elements at the worksite and elements at the operator's station;

FIG. 5 is a diagrammatic view to illustrate visual perception by a miniature virtual eye, and FIG. 6 is a diagrammatic view to illustrate visual perception by the operator when image magnification is employed;

FIG. 8 is a rear elevational view of the operator's station shown in FIG. 7;

FIG. 9 is a rear elevational view of the worksite shown in FIG. 7;

FIGS. 10 and 11 are fragmentary side elevational views of modified forms of operator's station and manipulator, respectively, having increased degrees of freedom;

FIG. 12 is a side elevational view of a modified form of operator's station wherein display means are positioned for direct viewing by the operator;

FIG. 13 is a rear elevational view of the modified form of operator's station shown in FIG. 12.

DESCRIPTION OF THE PREFERRED EMBODIMENTS

Figure 7:
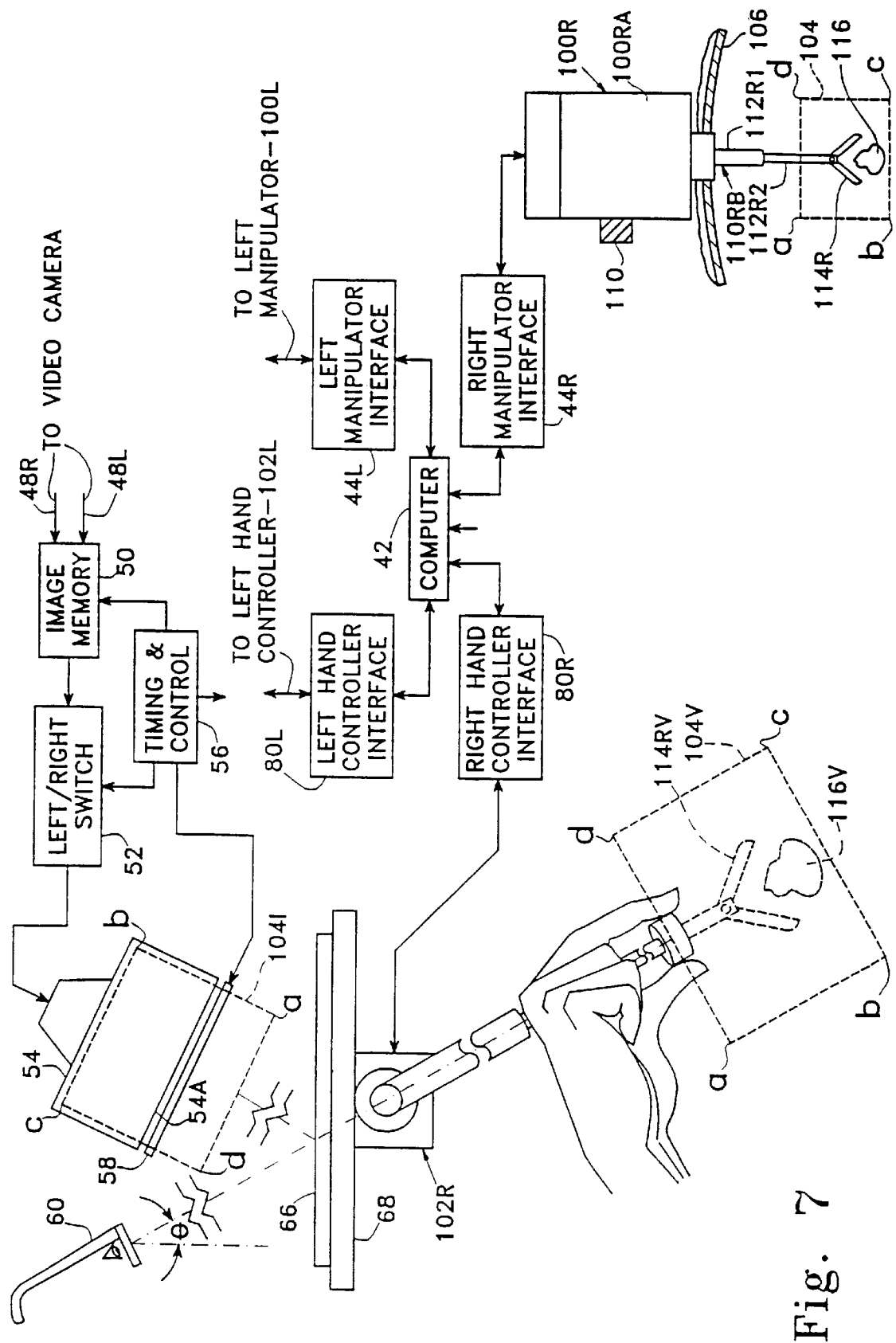
FIG. 7 is a diagrammatic view which is similar to that of FIG. 1 but showing the teleoperator system used for telepresence surgery.

Reference now is made to FIGS. 1–3 wherein the teleoperator system is shown in include an operator's station 20 (FIGS. 1 and 2) and worksite 22 (FIGS. 1 and 3). An operator 18 at the operator's station controls manipulator means 24 at the remote worksite. Manipulator means 24, comprising right and left manipulators 24R and 24L, respectively, are used for manipulating objects, such as object 26 which is shown located on a platform, or base, 28 within a workspace 30 shown in broken lines. For purposes of illustration only, and not by way of limitation, the right manipulator 24R is shown to comprise a housing 32R affixed to base 28 and from which housing telescopic arm 34R extends. The inner end 34R1 of arm 34R is mounted for pivotal movement in any pivotal direction using conventional mounting means. For example, the inner end of arm 34R may be mounted for pivotal movement about a horizontal pivot axis 36 which pivot axis, in turn, is adapted for pivotal movement about vertical axis 38.

Arm 34R includes telescopic inner section 34R1 and outer section 34R2, which outer section is adapted both for axial movement into and out of inner section 34R1 and for rotation about its longitudinal axis. An end effector 40R is carried at the outer end of the arm which, for purposes of illustration, is shown to comprise a gripper. Motor means, not shown, control pivotal movement of arm 34R about pivot axes 36 and 38, axial and rotary movement of outer arm section 34R2 along and about the longitudinal axis of the arm, and opening and closing of gripper 40R. The motor means, together with motor control circuits for control of the motors, may be included in housing 32R. The motors are under control of a computer 42 connected thereto through right manipulator interface 44R and the above-mentioned motor control circuits.

The left manipulator 24L is of substantially the same design as the right manipulator 24R and the same reference numerals, but with the suffix L instead of R, are sued to identify similar parts. For purposes of illustration, the left end effector 40L, shown in FIG. 3, is seen to comprise cutting blades which operate to cut in the manner of a pair of scissor blades.

The worksite is provided with a pair of video cameras 46R and 46L for viewing workspace 30 from different angles for production of stereoscopic signal outputs therefrom at lines 48R and 48L. The angle γ between the optical axes of the cameras shown in FIG. 3 is substantially equal to the operator's interocular viewing angle γ of an image of the workspace as shown in FIG. 2.

The video camera outputs at lines 48R and 48L are supplied to an image memory 50 for momentary storage of video fields of right and left images from the cameras. Fields of right and left images from image memory 50 are alternately supplied through left/right switch means 52 to visual display means 54, such as a television monitor, for alternate display of the two images at the face 54A of the monitor. Timing and control means 56 provide timing and control signals to various elements of the system, including elements included in the stereographic display system, for signal timing and control of the system. If digital storage means 50 are employed, then conversion of the camera signal outputs to digital signal form by analog to digital converter means prior to storage, and conversion of the digital signal output from left/right switch means to analog signal form in preparation for display at monitor 54 may be employed.

An electrooptical device 58 at the face of the display means 54 controls polarization of light received from display means 54 under control of a left/right synchronizing signal from timing and control unit 56. The left and right image fields are viewed by operator 18 wearing a pair of passive polarized glasses 60 having right and left polarizing elements 62 and 64 polarized in orthogonal directions. The polarization of light from display 54 through electrooptical device 58 is synchronized field by field such that the right field is occluded from the left eye and the left field is occluded from the right eye for stereographic viewing by the operator. Other means for stereographic viewing of left and right image fields are well known, including, for example, those using active stereographic glasses, which may be used in the practice of this invention to provide the operator with a stereoscopic view of the remote workspace.

The vertical deflection coil connections for monitor 54 are reversed, causing the monitor to scan from bottom to top thereby creating a top-to-bottom inverted image 30I of workspace 30. Letters a, b, c and d are used to identify corresponding corners of the workspace 30 and inverted workspace image 30I. The inserted workspace image 30I is viewed by the operator via a mirror 66 at the top of a table 68, which mirror inverts image 30I to return the image as viewed by the operator to an upright position. Looking downwardly in the direction of the mirror, the operator views a virtual image 30V of workspace 30. In accordance with one aspect of the present invention, the image viewed by the operator, which in the FIG. 1–3 embodiment comprises a virtual image, is located adjacent controller means 70 used by the operator for control of manipulator means 24 at the worksite.

Controller means 70 are shown located beneath the tale top 68 and include right and left controllers 72R and 72L for control of the respective right and left manipulators 24R and 24L. The right and left controllers are of substantially the same design so that a description of one applies to both. As with the manipulators, the suffixes R and L are used to distinguish elements of the right controller from those of the left controller. For purposes of illustration, and not by way of limitation, the right controller 72R is shown to comprise a housing 74R affixed to the bottom of table top 68 and from which hand-operated means 76R in the form of a telescopic control arm, or stick, extends.

The right and left control arms 76R and 76L are provided with the same degrees of freedom as the associated manipulator arms 34R and 34L, respectively. For example, the inner end of control arm 76R is mounted for pivotal movement about a horizontal pivot axis, corresponding to manipulator pivot axis 36, which axis, in turn, is adapted for pivotal movement about an intersecting vertical axis, corresponding to manipulator axis 38. Control arm 76R also includes inner section 76R1 and outer section 76R2, which outer section is adapted both for axial movement into and out of inner section 76R1 and for rotation about its longitudinal axis. It will be apparent that the control arm 76R is provided with the same four degrees of freedom as the associated manipulator arm 34R. Additionally, sensor means 78R are located adjacent the outer end of outer arm section 76R2 for use in controlling gripping action of gripper 40R. Similar sensor means 78L adjacent the outer end of control arm 76L are adapted for use in controlling operation of scissor blades 40L.

Right and left controllers 72R and 72L are included in a servomechanism system wherein mechanical motion of control arms 76R and 76L controls the position of manipulator arms 34R and 34L, and pressure on sensor means 78R and 78L controls opening and closing of end effectors 40R and 40L, respectively. In FIG. 1, right and left hand controller interfaces 80R and 80L, respectively, are shown for connection of the controllers to computer 42. Servomechanisms for control of mechanical motion oat a remote location are well known, including those which provide force and torque feedback from the manipulator to the hand-operated controller means. Any suitable prior rat servomechanism may be used in the practice of the present invention, with those incorporating force and torque feedback being particularly preferred for telepresence operation of the system. In the illustrated system, right and left microphones are included at the worksite, outputs from which microphones are amplified by right and left amplifiers and supplied to right and left speakers at the operator' station for providing a stereophonic sound output to provide the operator with an audio perspective present at the workspace. In FIG. 1, only the right channel of the stereophonic system is shown including right microphone 82R, right amplifier 86R and right speaker 88R. The left microphone and speaker are located directly behind the respective right microphone and speaker at the worksite and operator's control station as viewed in FIG. 1. Obviously, earphones may be provided for use by the operator in place of the speakers which would help to block out external noises at the operator's control station. Also, in FIG. 1 a light shield 54B at the monitor is shown for blocking direct viewing of the monitor face by the operator.

Reference now is made to FIG. 4 wherein a simplified diagrammatic view of the system illustrated in FIG. 1–3 is shown and wherein various lengths and angular positions are identified by reference characters. In FIG. 4, the optical path length between the cameras and a point F at the workspace is identified by reference character L. A corresponding path length between the operator's eyes and point F at the virtual image of the workspace is identified by the distance a+b, where a is the distance from the eyes of the operator to mirror 66, and b is the distance from the mirror to point F at the virtual image. Other dimensions shown include the height G of the cameras above the pivot point of manipulator arm 34R and corresponding height g of the operator's eyes above the pivot point of control arm 76R. With the control arm 76R at length d, the manipulator arm 34R adjusts to length D. Similarly, with the control arm 76R at an angle $\beta_A$ with the vertical, the manipulator arm 34R is positioned at the same angle from vertical. The angle from vertical at which the cameras view the workspace and the eyes view the virtual image of the workspace is identified by $\alpha$.

Between elements of the worksite and operator station, the following relationships pertain:

$$a+b=kL, \tag{1}$$

$$d=kD, \text{ and} \tag{2}$$

$$g=kG \tag{3}$$

where k is a scale factor constant.

When k equal 1 such that a+b=L, d=K and g=G, no scaling of worksite dimensions is required.

Any scale factor may be employed, the invention not being limited to full-scale manipulation. For example, the worksite can be small, including microscopic in size, in which case the optical parameters, including distance to object, interocular distance and focal length, and mechanical and dimensional parameters are appropriately scaled.

By using appropriate scaling and image magnification and force and torque feedback, and by locating the image 30V of the workspace 30 adjacent hand-operated control means 76R and 76L, the operator is provided with a strong sense of directly controlling the end effectors 40R and 40L. The operator is provided with a sense that the end effectors 40R and 40L and respective control arms 76R and 76L are substantially integral. This same sense of togetherness of the hand-operated control means and end effectors is not provided in prior art arrangements wherein the image viewed by the operator is not located adjacent the hand-operated control means. Even where the prior art includes stereoscopic viewing and force and torque feedback, there is a feeling of disconnectedness of the hand motions from the visual image object being worked upon. The present invention overcomes this sense of disconnectedness by locating the workspace image where the operator's hand appear to exercise direct control over the end effectors.

For small-scale manipulation, such as required for surgical applications, it is desired to replicate the visual experience that a miniature observer would have were he closely adjacent the actual worksite. In FIG. 5, the virtual eye 90 of a hypothetical miniature observer is shown viewing an actual workspace. Light from a source at a point X, Y, Z in the actual workspace produces a stimulus on the miniature observer's eye 90 at a point identified as X'/M. In FIG. 6, an eye 92 of an actual operator is shown viewing an enlarged image of the virtual workspace produced by means of a video camera 94 used to view the actual workspace. The illustrated camera includes a light-receiving lens 96 and solid state imaging device such as a charge-coupled-device (CCD) array 98 where the point light source at X, Y, Z is shown imaged at point $X_i$, $Y_i$, $Z_i$. With correct scaling, a corresponding light source is produced at point $MX_i$, $MY_i$, $MZ_i$ at either the real or apparent position of the face of the visual display which, due to stereoscopic operation of the system appears to the operator to originate from point MX, MY, MZ corresponding to point X, Y, Z at the actual workspace. At the retina of the actual eye 92, a stimulus is produced at point X' at proportionately the same position as point X'/M at eye 90 of the hypothetical observer. This relationship is ensured by selecting a correctly scaled camera distance and lens focal length such that the optical magnification $M_o = M/M_v$, where M is the desired overall magnification and $M_v$ is the video magnification. A typical video magnification, $M_v$, which equals the ratio of the CCD-array 98 width to the display width, is about 40.

Reference now is made to FIGS. 7 through 9 wherein a modified form of this invention is shown for medial use.

Here, right and left manipulators 100R and 100L are shown which are under control of right and left controllers 102R and 102L, respectively. Elements of the imaging system are substantially the same as those employed in the imaging system illustrated in FIGS. 1–3 described above except that an enlarged virtual image 104V of actual workspace 104 is provided for viewing by the operator. Also, servomechanism elements for connection of the right and left controllers 102R and 102L to the respective manipulators 100R and 100L are substantially the same as those described above with reference to FIGS. 1–3. In the illustrated arrangement, the right and left manipulators are of substantially the same construction as are the right and left controllers, such that a description of one manipulator and one controller applies to both. Again, suffixed R and L are used to distinguish between right and left elements thereof.

The manipulators include outer control sections 100RA and 100LA and insertion sections 100RB and 100LB, which insertion sections are adapted for insertion into a body cavity through cylindrical tubes, or cannulas, not shown. For purposes of illustration, the manipulators are shown inserted through the abdomen wall 106 of a subject. As is well understood, for laparoscopic surgical procedures, wall 106 is separated from internal organs by insufflation wherein a gas is introduced into the abdomen by any suitable means not shown. Manipulator motors and associated motor control circuits are contained in the outer control sections 100RA and 100LA of the manipulators for control of the insertion section. The manipulators, together with a laparoscope 108 for viewing organs within the cavity, are carried by a fixed rail 110 forming part of a surgical table upon which the subject is supported.

The insertion sections 100RB and 100LB of the manipulators may be of substantially the same design as manipulator arms 34R and 34L described above with reference to the FIGS. 1–3 embodiment. The insertion sections are of relatively small size for use inside the body. Insertion section 100RB includes telescopic inner section 112R1 and outer section 112R2, which outer section is adapted for both axial movement into and out of inner section 112R1 and for rotation about its longitudinal axis. End effectors 114R and 114L are carried at the outer ends of the respective right and left sections 112R2 and 112L2 for manipulation of organ 116. The inner section 112R1 is adapted for pivotal movement about intersecting perpendicular axes located substantially at point P where the insertion section intersects wall 106. Exclusive of operation of end effectors 114R and 114L the manipulator rams each are provided with four degrees of freedom, the same as in the embodiment shown in FIGS. 1–3. End effectors 114R and 114L simply may comprise, essentially, microsurgical instruments with their handles removed including, for example, retractors, electrosurgical cutters and coagulators, microforceps, microneedle holders, dissecting scissors, blades, irrigators, and sutures.

Laparoscope 108 for viewing the workspace 104 is shown comprising an outer operating section 108A and insertion section 108B. The outer end section 120 of insertion section 108B is axially and rotatably movable within the inner end 122 thereof, and is provided with a pair of image transmission windows 124, 124 for stereoscopic viewing of workspace 104. The laparoscope also is provided with illuminating means, not shown for illuminating the workspace, and with liquid inlet and outlet means, not shown, for flow of liquid past the windows. Video camera means within section 108A are responsive to light received through the viewing windows for generation of left and right electronic images at output lines 48R and 48L for connection to image memory 50. A magnified 3-dimensional image 104I is produced at display means 54 for viewing by the operator wearing cross-polarized glasses 60 via mirror 66. As with the embodiment shown in FIGS. 1–3, a virtual image 104V of the workspace 104 is produced adjacent control arms 130R and 130L of controllers 102R and 102L. Control arms 130R and 130L are of the same type as control arms 76R and 76L included in the FIGS. 1–3 embodiment described above. They include telescopic inner and outer sections 132R1 and 132R, and 132L1 and 132L2. Sensor means 134R and 134L located adjacent the outer ends of the control arms control operation of end effectors 114R and 114L, respectively, in the manner described above with reference to FIGS. 1–3. It here will be noted that the angle from vertical at which the image is viewed by the operator need not equal the angle from vertical at which the object is viewed by the cameras. In the arrangement illustrated in FIGS. 7–9, the operator is shown to view the image 104V at an angle θ from vertical (FIG. 7) whereas the object 116 is shown as viewed directly downwardly. With no external reference, the sense of vertical within a body is not particularly great, and no confusion is produced in the mind of the operator as a result of the different observer and camera viewing angles relative to vertical.

With the FIGS. 7–9 embodiment, not only is a magnified virtual image 104V of the workspace provided for viewing by the operator, but control arms 130R and 130L of greater length than the length of the manipulator insertion sections 100RB and 100LB are employed. Servomechanism scaling of axial movement of the telescopic control arms is provided such that axial extension or retraction thereof results in a smaller extension or retraction of the telescopic insertion sections. Angular pivotal motion of the control arms 130R and 130L produces the same angular pivotal motion of insertion sections 100RB and 100LB, and rotational movement of the end sections 132R2 and 132L2 of the control arms produces the same rotational motion of end sections 112R2 and 112L2 of the insertion sections of the right and left manipulators, without scaling. This embodiment of the invention, with its magnified image, is of particular use in the area of microsurgery, and especially in those cases where the surgeon cannot reach an area by hand because of size constraints.

The present invention is not limited to use with manipulators having any particular number of degrees of freedom. Manipulators with different degrees of freedom which are well known in the art may be used in the practice of this invention. In FIGS. 10 and 11, to which reference now is made a controller 140 and manipulator 142, respectively, are shown which include a wrist joint to provide the same with additional freedom of movement. The illustrated controller 140 includes a housing 144 affixed to the bottom of table top 68 upon which table mirror 66 is located. An enlarged virtual image 146V of actual workspace 146 is provided adjacent the operator's hand 148 viewable by the operator when looking downwardly onto the mirror 66 in a manner described above.

A control arm 150L comprising inner and outer sections 150L1 and 150L2, respectively, is mounted within housing 144 for pivotal movement in any pivotal direction as indicated by intersecting double-headed arrows 152 and 154. The outer section 150L2 is adapted for axial movement into and out of inner section 150L1 in the direction of double-headed arrow 156. It also is adapted for rotation about its longitudinal axis in the direction of double-headed arrow 158. In this embodiment, the control arm includes an end section 160 pivotally attached to outer section 150L2 by wrist joint 162 for pivotal movement in the direction of double-headed arrow 164. End section 160 comprises axially aligned inner and outer sections 160A and 160B, the outer section 160B of which is rotatable about its longitudinal axis in the direction of double-headed arrow 166. As with the above-described arrangements, sensor means 168 are located adjacent the free end of the control arm for operation of an end effector 170 at manipulator 142 shown in FIG. 11.

Referring to FIG. 11, end effector 170 is shown to comprise a pair of movable jaws attached to a wrist 172 comprising axially aligned links 172A and 172B. Outer link 172B is rotatable about its longitudinal axis relative to inner link 172A by motor means, not shown, in the direction of double-headed arrow 166M in response to rotation of section 160B of the hand-operated control unit in the direction of arrow 166. Wrist link 172A is pivotally attached to manipulator forearm 174 for pivotal movement in the direction of double-headed arrow 164M in response to pivotal movement of end section 160 of the hand-operated control means about pivot axis 162. Forearm 174 is longitudinally axially movable in the direction of double-headed arrow 156M in response to axial movement of outer section 150L2 of control arm 150L in the direction of double-headed arrow 156. It also is rotatable about its longitudinal axis in the direction of double-headed arrow 158M in response to rotation of outer section 150L2 of control arm 150L in the direction of double-headed arrow 158. Additionally, it is pivotally movable about point 176 in the directions of double-headed arrows 152M and 154M in response to pivotal movement of control arm 150L in the directions of double-headed arrows 152 and 154, respectively. For biomedical use, such as remote laparoscopic surgery, pivot point 176 is substantially located at the level of abdominal wall 178 through which the manipulator extends. In FIG. 11, manipulator arm 174 is shown extending through a cannula 180 which penetrates the abdominal wall.

The outer operating end of the manipulator is adapted for attachment to a supporting rail, not shown, of the surgery table upon which the subject is supported. It includes an end effector drive motor 182 for opening and closing of gripper 170. Wrist drive motor 184 controls pivotal movement of wrist 172 in the direction of double-headed arrow 164M, and extension drive motor 186 controls axial movement of manipulator arm 174 in the direction of double-headed arrow 156M. Forearm pivotal control motors and linkages, identified generally by reference numeral 188, provide for pivotal movement of arm 174 about pivot point 176 in the directions of arrows 152M and 154M. Pivotal motion about point 176 is provided by simultaneous lateral movement of the outer operating end of the manipulator and pivotal movement of arm 174. Movements are coordinated such that the center of rotation of forearm 174 is fixed in space at point 176 at the level of the abdominal wall.

Controller 140 and manipulator 142 are included in a system such as shown in FIGS. 7, 8 and 9 which includes a second controller and manipulator for use by the operator's right hand, and associated servomechanism means of any suitable type, not shown, for remote control of the manipulators by the hand-operated controllers. Video camera means at the worksite, such as shown in FIG. 9, together with display means, such as shown in FIG. 7, are employed for providing the operator with an image of the workspace at a location adjacent the left and right hand-operated control means. By using manipulators with a wrist joint, an added degree of freedom is provided for increased maneuverability and usefulness thereof. However, as noted above, the present invention is not limited to use with manipulators with any particular degree of freedom.

Reference now is made to FIGS. 12 and 13 wherein a modified form of this invention is shown which provides for direct viewing of a 3-dimensional image 240I of a workspace, not shown. In FIGS. 12 and 13, only the operator's station is shown, which includes right and left controllers 242R and 242L and associated right and left hand-operated means 244R and 244L which may be of the same type as controllers and control arms described above. The operator's station is adapted for remote control of manipulators which also may be of the above-described type. The 3-dimensional image 240I of the workspace is provided by visual display means 246 in conjunction with electrooptical device 58 at the face of the display means and cross-polarized glasses 60 worn by the operator, to which display means left and right video fields from left and right video cameras that view the workspace are alternately supplied, all in the manner described in detail above. End effector and object images 248 and 250, respectively, are shown within the workspace image as viewed by video cameras at the worksite. The display means 246 is located adjacent the left and right hand-operated means 244R and 244L for direct viewing by the operator. With this arrangement, the end effector and object images together with the hand-operated means 244R and 244L are simultaneously viewable by the operator. Since the hand-operated means also are visible, the operator is provided with a visual sense of connection between the end effector means and hand-operated means whereby they appear substantially as being integral.

Figure 14:
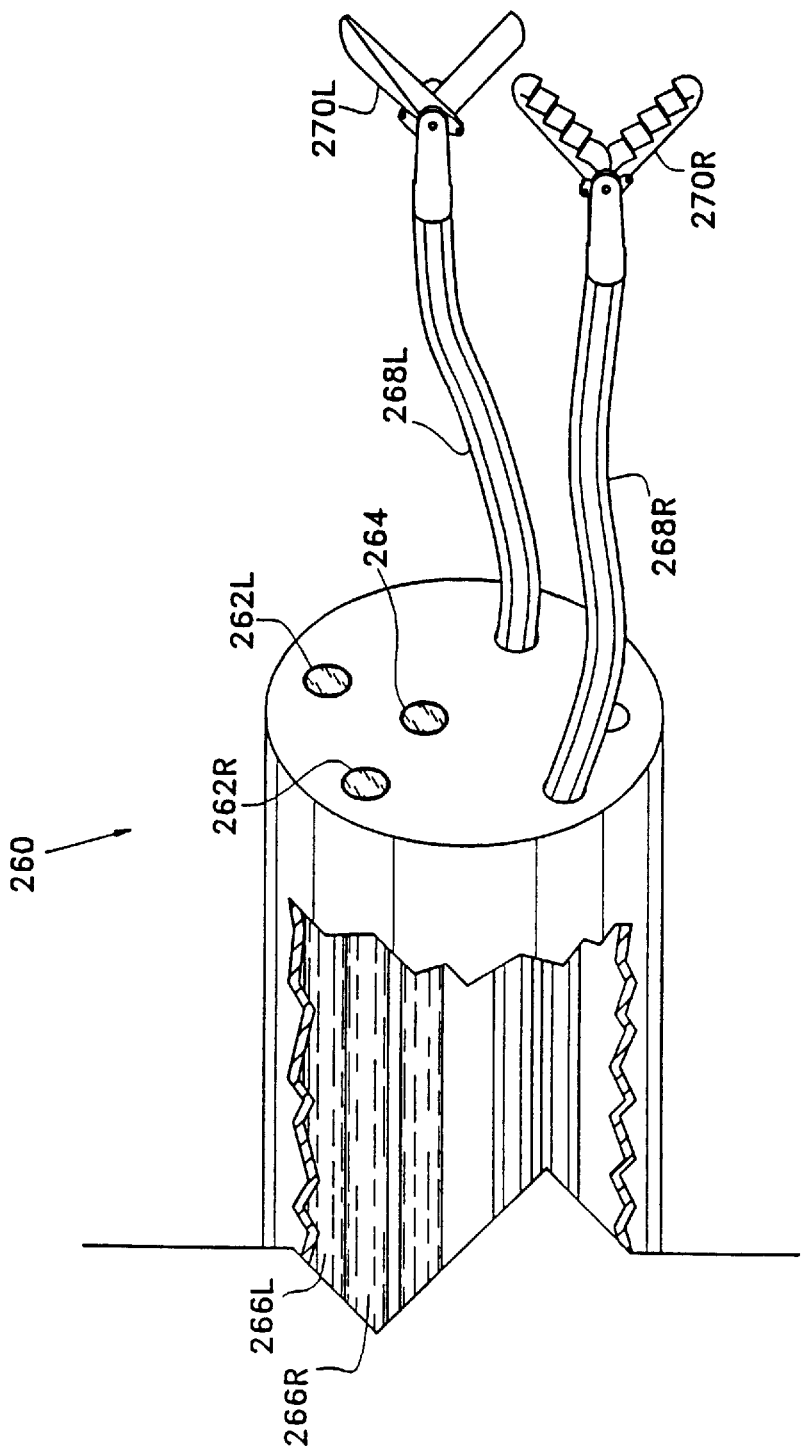
FIG. 14 shows a fragmentary portion of the insertion portion of an endoscope for use with the present invention.

Reference now is made to FIG. 14 wherein the distal end portion, or tip, 260 of the insertion section of an endoscope is shown which is of substantially the same type as shown in the above-mentioned publication entitled "Introduction to a New Project for National Research and Development Program (Large-Scale Project) in FY 1991" which endoscope may be used in the practice of the present invention. The insertion end of the endoscope includes a pair of spaced viewing windows 262R and 262L and an illumination source 264 for viewing and illuminating a workspace to be observed. Light received at the windows is focused by objective lens means, not shown, and transmitted through fiber-optic bundles to a pair of cameras at the operating end of the endoscope, not shown. The camera outputs are converted to a 3-dimensional image of the workspace which image is located adjacent hand-operated means at the operator's station, now shown. Right and left steerable catheters 268R and 268L pass through accessory channels in the endoscope body, which catheters are adapted for extension from the distal end portion, as illustrated. End effectors 270R and 270L are provided at the ends of the catheters which may comprise conventional endoscopic instruments. Force sensors, not shown, also are inserted through the endoscope channels. Steerable catheters which include control wires for controlling bending of the catheters and operation of an end effector suitable for use with this invention are well know. Control motors for operation of the control wires are provided at the operating end of the endoscope, which motors are included in a servomechanism of a type described above for operation of the steerable catheters and associated end effectors from a remote operator's station. As with the other embodiments, the interfacing computer in the servomechanism system remaps the operator's hand motion into the coordinate system of the end effectors, and images of the end effectors are viewable adjacent the hand-operated controllers in a manner described above. With this embodiment, the operator has the sensation of reaching through the endoscope to put his hands directly on the end effectors for control thereof. Endoscopes of different types may be employed in this embodiment of the invention so long as they include one or more accessory channels for use in control of end effector means, and suitable viewing means for use in providing a visual display of the workspace. For example, gastric, colonscopic, and like type, endoscopes may be employed.

The invention having been described in detail in accordance with requirements of the Patent Statutes, various other changes and modifications will suggest themselves to those skilled in this art. For example, as noted above, the invention may include the use of tactile feedback to provide the subtle sensations for palpation and for manipulating tissues and instruments. To provide this feedback, tactile sensor arrays may be included on the end effectors which are coupled to tactile sensor stimulator arrays on the hand-operated control means, which reproduce the tactile sensation on the operator's hand. A variety of transduction technologies for teleoperator tactile sensing are known including resistive/ conductive, semiconductor, piezoelectric capacitive and photoelectric. Hand-operated control means and manipulators of different types may be employed using a wide variety of well-known mechanisms and electromechanical elements including, for example, gimbals, linkages, pulleys, cables, drive belts and band, gear, optical or electromagnetic position encoders, and angular and linear motors. Force feedback to the operator requires use of body contact with hand-operated control means. Both hand grip type hand controllers such as those illustrated, and control brace type hand controllers are well adapted for use with the present invention for force feedback to the operator. Control brace hand controllers include use of structures with positive sensors mounted on the operator at joints for measuring joint angles. Force feedback then can be applied to each joint. Similarly, light fabric gloves with variable-resistance or fiber-optic flex sensors mounted on the joints for measuring bending of individual fingers may be used. Gloves of this type also may be provided with force feedback to provide for telepresence interaction with real objects. Regardless of the type of hand-operated control means employed, an image of the workspace is produced adjacent thereto to provide the operator with a sense that the end effector means and hand-operated control means are substantially integral. Also, as noted above, servomechanisms of many different types are well known in the robotic and teleoperator system arts, and the invention is not limited to any particular type. Those that include force and torque feedback to the operator are preferred to contribute to a telepresence sense of operation. In addition, many different means for producing a stereoscopic image of the workspace are known. For example, instead of using two cameras, a single camera may be employed together with switched cross-polarizing elements in the image receiving path. In this case, a pair of spaced stereoscopic lenses are used for viewing the workspace from different angles and providing first and second images thereof to the camera. In the FIG. 9 arrangement, wherein a laparoscope is shown, other types of endoscopes may be used for viewing the workspace. As noted above, the invention is not limited to any particular application or use. In the biomedical field, uses include, for example, open surgery, including surgery from a remote location, microsurgery, and minimum invasive surgery such as laparoscopic and endoscopic surgery. Laboratory use including microscopic manipulation also is contemplated. Industrial use of the invention include, for example, hazardous materials handling, remote operations, microassembly, and the like. Military and undersea use of the teleoperator system of this system are apparent. It is intended that the above and other such changes and modifications shall fall within the spirit and scope of the invention defined in the appended claims.

I claim:

1. An endoscopic surgical instrument comprising a control section and an insertion section wherein:

the insertion section is insertable into a patient through a small incision to a location adjacent a worksite in the patient;

the insertion section comprises a rigid forearm link, a wrist link and an end effector wherein:

the forearm link has a proximal end, a distal end and a forearm axis extending longitudinally from the proximal end of the forearm link to the distal end of the forearm link;

the wrist link has a proximal end and a distal end and a wrist axis extending from the proximal end of the wrist link to the distal end of the wrist link;

the proximal end of the forearm link is connected to the control section, the distal end of the forearm link is connected to a pivotal wrist joint; and the proximal end of the wrist link is connected to the pivotal wrist joint and the distal end of the wrist link is connected to the end effector;

and the control section comprises a plurality of control motors and linkages to operate the insertion section with at least five degrees of freedom including:

insertion and retraction of the forearm link along the forearm axis and through the small incision;

rotation of the forearm link about the forearm axis;

pivotal motion of the forearm link about a first pivotal axis and a second pivotal axis which are perpendicular to each other and intersect the forearm axis at a pivot point between the proximal end of the forearm link and the distal end of the forearm link adjacent the small incision, wherein such pivotal motion of the forearm link avoids lateral movement of the forearm link at the pivot point; and pivotal motion of the wrist link relative to the forearm link.

2. The endoscopic surgical instrument as described in claim 1 wherein the wrist link comprises an inner link and an outer link and wherein the control section operates the insertion section with at least six degrees of freedom including movement of the outer link of the wrist link relative to the inner link of the wrist link.

3. The endoscopic surgical instrument as described in claim 2 wherein the outer link of the wrist link and the inner link of the wrist link are axially aligned and wherein the control section rotates the outer link relative to the inner link.

4. The endoscopic surgical instrument as described in claim 1 wherein the end effector comprises a first element and a second element and wherein the control section moves the first element relative to the second element.

5. The endoscopic surgical instrument as described in claim 2 wherein the end effector comprises a first element and a second element and wherein the control section moves the first element relative to the second element.

6. The endoscopic surgical instrument as described in claim 1 wherein the end effector comprises a surgical instrument head selected from the group of retractors, electrosurgical cutters, electrosurgical coagulators, forceps, needle holders, scissors, blades and irrigators.

7. The endoscopic surgical instrument as described in claim 1 wherein the control section is fixed to a support rail of a surgical table for support of a surgical manipulator during surgery.

8. A surgical method for endoscopic surgery comprising the steps of:

providing an endoscopic surgical instrument comprising a control section and an insertion section;

inserting the insertion section into a patient through a small incision to a location adjacent a worksite inside the patient, wherein the insertion section comprises a rigid forearm link, a wrist link and an end effector, and wherein:

the forearm link has a proximal end, a digital end and a forearm axis extending longitudinally from the proximal end of the forearm link to the distal end of the forearm link;

the wrist link has a proximal end and a distal end and a wrist axis extending from the proximal end of the wrist link to the distal end of the wrist link;

the proximal end of the forearm link is connected to the control section, the distal end of the forearm link is connected to a pivotal wrist joint;

the proximal end of the wrist link is connected to the pivotal wrist joint and the distal end of the wrist joint is connected to the end effector; and the forearm link is inserted distally along the forearm axis through the small incision;

operating a servomechanism to rotate the forearm link about the forearm axis;

operating the servomechanism to pivot the forearm link about a first pivotal axis and a second pivotal axis which are perpendicular to each other and intersect the forearm axis at a pivot point, the pivot point disposed between the proximal end of the forearm link and the distal end of the forearm link and adjacent the small incision, wherein such pivotal operation of the forearm link avoids lateral movement of the forearm link at the pivot point;

operating the servomechanism to pivot the wrist link relative to the forearm; and manipulating human tissue with the end effector at the worksite inside the patient.

9. The method as described in claim 8 wherein:

the endoscopic surgical instrument providing step comprises providing a surgical manipulator with a wrist link which comprises an inner link and an outer link; and the method comprises the additional step of operating the servomechanism to move the outer link of the wrist link relative to the inner link of the wrist link.

10. The method as described in claim 9 wherein:

the surgical manipulator providing step comprises axially aligning the outer link of the wrist link; and the step of moving the outer link of the wrist link relative to the inner link of the wrist link comprises the step of operating the servomechanism to rotate the outer link relative to the inner link.

11. The method as described in claim 8 wherein:

the end effector comprises a surgical instrument having a first element and a second element; and the method comprises the additional step of operating the servomechanism to move the first element relative to the second element.

12. The method as described in claim 9 wherein:

the end effector comprises a surgical instrument having a first element and a second element; and the method comprises the additional step of operating the servomechanism to move the first element relative to the second element.

13. The surgical method as described in claim 8 wherein:

the end effector comprises a surgical instrument head selected from the group consisting of retractors, electrosurgical cutters, electrosurgical coagulators, forceps, needle holders, scissors, blades and irrigators; and the step of manipulating human tissue comprises the step of actuating the surgical instrument head.

14. The surgical method as described in claim 8 further comprising the step of mounting the control section on a support rail of a surgical table for support of a surgical manipulator during surgery.

15. An endoscopic surgical instrument comprising an insertion section and a control section wherein:

the insertion section is insertable into a patient through a small incision to a location adjacent a worksite in the patient;

the insertion section comprises a rigid forearm link, a wrist link and an end effector wherein:

the forearm link has a proximal end, a distal end and a forearm axis extending longitudinally from the proximal end of the forearm to the distal end of the forearm;

the wrist link has a proximal end and a distal end and a wrist axis extending from the proximal end of the forearm to the distal end of the forearm;

the proximal end of the forearm link is connected to the control section, the distal end of the forearm link is connected to a pivotal wrist joint; and the proximal end of the wrist link is connected to the pivotal wrist joint and the distal end of the wrist joint is connected to the end effector;

and the control section comprises:

means for inserting and retracting the forearm link along the forearm axis and through the small incision;

means for rotating the forearm link about the forearm axis;

means for pivoting the forearm link about a first pivotal axis and a second pivotal axis which are perpendicular to each other and intersect the forearm axis at a pivot point between the proximal end of the forearm link and the distal end of the forearm link adjacent the small incision, wherein such pivotal means avoids lateral movement of the forearm link at the pivot point; and means for pivoting the wrist link relative to the forearm link so as to control the angle between the forearm axis and the wrist axis.

16. The endoscopic surgical instrument as described in claim 15 wherein the wrist link comprises an inner link and an outer link and wherein the control section further comprises means for moving the outer link of the wrist link relative to the inner link of the wrist link.

17. The endoscopic surgical instrument as described in claim 16 wherein the outer link of the wrist link and the inner link of the wrist link are axially aligned and wherein the control section further comprises means for rotating the outer link relative to the inner link.

18. The endoscopic surgical instrument as described in claim 15 wherein the end effector comprises a first element and a second element and wherein the control section further comprises means for moving the first element relative to the second element.

19. The endoscopic surgical instrument as described in claim 16 wherein the end effector comprises a first element and a second element and wherein the control section further comprises means for moving the first element relative to the second element.

20. The endoscopic surgical instrument as described in claim 17 wherein the end effector comprising a surgical instrument head selected from the group of retractors, electrosurgical cutters, electrosurgical coagulators, forceps, needle holders, scissors, blades and irrigators.

21. The endoscopic surgical instrument as described in claim 17 wherein the control section further comprises means for mounting the control section on a support rail of a surgical table for supporting the endoscopic surgical instrument during a surgical procedure.

22. A minimally invasive surgery system comprising:
a surgical station including a manipulating linkage supporting an actuatable end effector, the manipulator including an elongate rigid member having a proximal end and a distal end, wherein a joint is disposed between the distal end of the member and the end effector;
a control station including an actuatable handle and a movable controller; and
a servomechanism coupling the handle to the end effector so that actuation of the handle effects actuation of the end effector to manipulate tissue at an internal surgical site within a patient body, wherein the servomechanism moves the end effector within the internal surgical site in response to movement of the controller by pivoting the member about a first pivotal axis and a second pivotal axis which are perpendicular to each other and intersect at an insertion point between the proximal and distal ends of the member, wherein such pivotal movement of the member avoids lateral movement of the member at the insertion point, and by articulating the joint distally of the insertion point and within the patient body.

23. The minimally invasive surgery system of claim 22, wherein the member comprises a rigid forearm link defining a forearm axis extending longitudinally from the proximal end of the forearm to the distal end of the forearm, and further comprising:
a wrist link pivotally connected to the distal end of the forearm so as to pivot about a first axis which is generally perpendicular to the longitudinal forearm axis of the forearm link;
wherein the end effector comprises an end effector member coupled to the wrist link by the joint so as to move about a second axis which is generally perpendicular to the first axis.

24. The minimally invasive surgery system of claim 23, wherein said end effector includes a pair of jaw elements pivotally coupled to the wrist link.

25. The minimally invasive surgery system of claim 22, wherein the servomechanism drives the proximal end of the member laterally relative to an axis of the member in first and second degrees of freedom, and wherein the servomechanism drives the proximal end of the member axially relative to the axis in a third degree of freedom in response to movement of the controller.

26. The minimally invasive surgery system of claim 25, wherein the servomechanism pivots the end effector so as to orient the end effector within the patient body with a plurality of degrees of freedom relative to the member.

27. The minimally invasive surgery system of claim 22, wherein the control station includes a station housing, wherein the controller comprises a linkage coupling the handle to the station housing, wherein the servomechanism repositions the end effector in the internal surgical site in response to repositioning of the handle in a station workspace, and wherein the servomechanism reorients then end effector in the internal surgical site in response to reorientation of the handle in the station workspace.

28. The minimally invasive surgery system of claim 27, wherein the surgical station includes an endoscope oriented toward the end effector, wherein the control station includes a display coupled to the endoscope so as to produce an image of the end effector, and wherein the display is oriented relative to the handle and the servomechanism is programmed so that the image of the endoscope as viewed by an operator and the handle as held by a hand of the operator appear to the operator to define an integral body during positional and orientational movements of the handle and the end effector.

29. The minimally invasive surgery system of claim 22, wherein the end effector comprises a surgical instrument head selected from the group consisting of retractors, electrosurgical cutters, electrosurgical coagulators, forceps, needle holders, scissors, blades, and irrigators.

30. A minimally invasive surgery system comprising:
a surgical station including a manipulator linkage supporting an end effector so that the end effector can move in three dimensions, the manipulator including an elongate rigid member having a proximal end and a distal end, the proximal end of the member movable in a plurality of proximal degrees of freedom, wherein a joint is disposed between the distal end of the member and the end effector, the joint providing a plurality of distal degrees of freedom;
a control station including an actuatable handle and a movable controller, the actuatable handle movable in a three dimensional station workspace; and
a servomechanism coupling the handle to the end effector so that actuation of the handle effects actuation of the end effector, the servomechanism coupled to the manipulator so that movement of the controller in the three dimensional space effects movement of the end effector in the surgical site by driving the proximal end in the proximal degrees of freedom, by pivoting the member about a first pivotal axis and a second pivotal axis which are perpendicular to each other and intersect at an insertion point between the proximal end and the distal end, wherein such pivotal movement of the member avoids lateral movement of the member at the insertion point, and by articulating the joint about the distal degrees of freedom.

31. A minimally invasive surgery method comprising:
inserting a surgical end effector into an internal surgical site of a patient body through a percutaneous penetration, the end effector attached to a rigid member by a joint;
actuating the end effector to manipulate tissue in response to actuation of a handle of a control station;
moving the end effector at the surgical site with a servomechanism in response to movement of the handle by driving a proximal end of the member outside the patient body with the servomechanisms and by articulating the joint inside the patient body with the servomechanism, wherein the member pivots about a first pivotal axis and a second pivotal axis which are perpendicular to each other and intersect at the percutaneous penetration between the proximal end of the member and a distal end of the member when the end effector is moved by the servomechanism so as to avoid lateral movement of the member relative to the percutaneous penetration.

32. The minimally invasive surgery method of claim 31, wherein the member comprises a rigid forearm, wherein a wrist member is pivotally connected to the forearm member by the joint so as to pivot about a firs axis, and wherein the end effector comprises a plurality of end effector elements movably coupled to the wrist member so as to move about a second axis that is generally perpendicular to the first axis;

wherein the moving step is performed by manually pivoting a wrist-pivoting element of a control assembly by cause the wrist member to pivot correspondingly about the distal forearm end and along the first axis; and wherein the end effector actuation step is performed by manually actuating the handle to cause the end effector elements to move about the second axis.

* * * * *